(12) United States Patent
Yamanari et al.

(10) Patent No.: US 9,584,098 B2
(45) Date of Patent: Feb. 28, 2017

(54) SAMPLE CLOCK GENERATOR FOR OPTICAL TOMOGRAPHIC IMAGING APPARATUS, AND OPTICAL TOMOGRAPHIC IMAGING APPARATUS

(71) Applicant: TOMEY CORPORATION, Nagoya-shi, Aichi (JP)

(72) Inventors: Masahiro Yamanari, Aichi (JP); Keiichiro Okamoto, Aichi (JP)

(73) Assignee: TOMEY CORPORATION, Nagoya-Shi (JP)

( * ) Notice: Subject to any disclaimer, the term of this patent is extended or adjusted under 35 U.S.C. 154(b) by 26 days.

(21) Appl. No.: 14/562,850

(22) Filed: Dec. 8, 2014

(65) Prior Publication Data

US 2015/0162900 A1 Jun. 11, 2015

(30) Foreign Application Priority Data

Dec. 10, 2013 (JP) ................................. 2013-255137

(51) Int. Cl.
*G01B 9/02* (2006.01)
*H03K 3/013* (2006.01)
(Continued)

(52) U.S. Cl.
CPC .......... *H03K 3/013* (2013.01); *G01B 9/02004* (2013.01); *G01B 9/02069* (2013.01);
(Continued)

(58) Field of Classification Search
CPC ............ G01B 9/02004; G01B 9/02069; G01B 9/02091
(Continued)

(56) References Cited

U.S. PATENT DOCUMENTS 6,020,963 A * 2/2000 DiMarzio .......... G01N 21/4795
356/491
2008/0165366 A1* 7/2008 Schmitt ................ A61B 5/0066
356/519
(Continued)

FOREIGN PATENT DOCUMENTS

JP 5269809 8/2013
JP 2013-181790 9/2013

OTHER PUBLICATIONS

European Search Report from corresponding EP Appln. No. 14306992.0 dated Apr. 14, 2015.
(Continued)

*Primary Examiner* — Jonathan Hansen
(74) *Attorney, Agent, or Firm* — Grossman, Tucker, Perreault & Pfleger, PLLC

(57) ABSTRACT

A sample clock generator includes a first optical path and a second optical path through which input lights are guided, an optical phase shifter to shift a phase of the input light guided through the first optical path, an interference-light generating unit to combine a phase-shifted input light and the input light guided through the second optical path to thereby generate an interference light for sample clock, a splitting unit to split the interference light for sample clock into two split lights having different phases, one light receiving unit to at least receive one split light from among the two split lights having different phases, the other light receiving unit to at least receive the other split light, a signal generating unit to generate a sample clock signal based on signals outputted from the one light receiving unit and the other light receiving unit.

11 Claims, 8 Drawing Sheets

(51) Int. Cl.
*H03K 3/42* (2006.01)
*G02F 1/21* (2006.01)
*G02B 27/10* (2006.01)
*H01L 31/0232* (2014.01)

(52) U.S. Cl.
CPC ......... *G01B 9/02091* (2013.01); *G02B 27/10* (2013.01); *G02F 1/21* (2013.01); *H01L 31/02325* (2013.01); *H03K 3/42* (2013.01)

(58) Field of Classification Search
USPC ........................................ 356/479, 497, 491
See application file for complete search history.

(56) References Cited

U.S. PATENT DOCUMENTS

| 2008/0175465 | A1 | | 7/2008 | Jiang et al. | |
|---|---|---|---|---|---|
| 2013/0021616 | A1 | * | 1/2013 | Kimura | G02B 21/0072 356/491 |
| 2014/0176963 | A1 | * | 6/2014 | Kemp | G01B 9/02004 356/497 |

OTHER PUBLICATIONS

Jiefeng Xi et al., "Generic real-time uniform K-space sampling method for high-speed swept-source optical coherence tomography", Optics Express, vol. 18, No. 9, Apr. 26, 2010, pp. 9511-9517.

* cited by examiner

SAMPLE CLOCK GENERATOR FOR OPTICAL TOMOGRAPHIC IMAGING APPARATUS, AND OPTICAL TOMOGRAPHIC IMAGING APPARATUS

CROSS-REFERENCE TO RELATED APPLICATIONS

This application claims the benefit of Japanese Patent Application No. 2013-255137 filed Dec. 10, 2013 in the Japan Patent Office, the disclosure of which is incorporated herein by reference.

BACKGROUND

The present invention relates to a sample clock generator for an optical tomographic imaging apparatus suitably applied in an optical coherence tomography using an optical frequency-swept laser, and an optical tomographic imaging apparatus.

An optical coherence tomography (hereinafter referred to as "OCT") is designed to measure a tomographic image of a living body using optical interferometry. Particularly, the OCT is widely used to acquire a two- or three-dimensional tomographic image of a cornea, a retina, and so on in ophthalmology. Several basic systems exist for such an OCT, and a technique called swept-source OCT, hereinafter referred to as "SS-OCT", is receiving attention above all.

In the SS-OCT, a light in which an optical frequency has been swept at high speed is emitted from a light source, and the light is radiated on an object to be measured, such as an eyeball. A scattered light from the object to be measured is detected by means of an interferometer. A detected raw signal (interference signal) is an interference spectrum, and by Fourier-analyzing the interference signal, a scattered light intensity distribution can be obtained that is resolved in a depth direction of the object to be measured. Such scattered light intensity distribution resolved in the depth direction of the object to be measured is generally called an A-scan OCT signal. Further, by laterally scanning a beam radiated on the object to be measured, a two-dimensional scattered light intensity distribution or a three-dimensional scattered light intensity distribution can be obtained.

Generally, in the SS-OCT, sampling of the interference signal is performed at high speed. It is preferred that such sampling is performed at equal optical frequency intervals. For example, it is known that, if the sampling is not performed at equal optical frequency intervals (at even frequency intervals with respect to the optical frequency), a distortion is generated in the A-scan OCT signal to thereby deteriorate the resolution significantly.

As a method for performing a sampling at equal optical frequency intervals, a method in which an optically-generated sample clock is used is known. In this method, aside from the interferometer used in the OCT, a Mach-Zehnder interferometer is structured, for example (see Japanese Unexamined Patent Application Publication No. 2013-181790 and Published Japanese Patent No. 5269809, for example). An output of the Mach-Zehnder interferometer is a sine wave at equal intervals with respect to the frequency of an input light. Therefore, the output of the Mach-Zehnder interferometer (an interference signal for clock) can be used as the above-described sample clock. Such a sample clock is often called a k-clock.

SUMMARY

In the SS-OCT, an interference signal for clock, which is a basis of the k-clock, is generated using a light emitted from a wavelength-swept light source that sweeps an optical frequency. Thus, the k-clock is affected directly by performance of the wavelength-swept light source. Generally, when the wavelength-swept light source of the SS-OCT is used, the greater a difference in optical path length in the interferometer is, the smaller an amplitude of the interference pattern is. Such a property also applies to the interferometer that generates a signal for clock to be inputted into the k-clock. That has caused a problem that, when a high-frequency k-clock is attempted to be generated, the amplitude of the interference pattern becomes smaller and generation of a high-frequency k-clock is made difficult.

In order to solve the above-described problem, a method for doubling a frequency of a k-clock electrically is suggested, as disclosed in Published Japanese Patent No. 5269809. An electrical phase shifter is used in this method, and a specified frequency or a specified range of frequency can be doubled electrically.

However, interference patterns of the interference signal for clock includes a wide range of frequency beyond the above-described specified range. Since a phase shift amount by the electrical phase shifter depends on the frequency of the interference signal for clock, if the interference patterns include a wide range of frequency beyond the specified range as above, it becomes difficult for the electrical phase shifter to provide the same phase shift amount for all frequency components. As a result, a problem has arisen that, when the frequency of the k-clock is doubled using the electrical phase shifter, it is difficult to generate the k-clock frequency with equal intervals.

The present invention has been made to solve the above-described problems. An object of the present invention is to provide a sample clock generator for an optical tomographic imaging apparatus capable of multiplying a frequency of a sample clock signal, and an optical tomographic imaging apparatus.

In order to achieve the above-described object, the present invention provides the following means.

A sample clock generator for an optical tomographic imaging apparatus of the present invention is configured to receive a frequency-swept input light emitted from a light source and to generate a sample clock signal. The sample clock generator includes an interference optical system and an operation unit. The interference optical system at least includes a first optical path through which part of the input light is guided; a second optical path through which other part of the input light is guided; an optical phase shifter to shift a phase of the input light guided through the first optical path; an interference-light generating unit to combine the input light guided through the first optical path and phase-shifted and the input light guided through the second optical path, to thereby generate an interference light for sample clock; and a splitting unit to split the interference light for sample clock into one split light and the other split light having different phases. The operation unit at least includes one light receiving unit to at least receive the one split light; the other light receiving unit to at least receive the other split light; and a signal generating unit to generate the sample clock signal based on signals outputted from the one light receiving unit and the other light receiving unit.

According to the sample clock generator for an optical tomographic imaging apparatus of the present invention, the frequency of the sample clock signal generated by the signal generating unit can be multiplied while inhibiting an influence of a frequency of the input light on the frequency of the sample clock signal, by shifting the phase of the input light guided through the first optical path with the optical phase shifter.

The phase of the input light shifted by the optical phase shifter is less affected by the frequency of the input light, which is an input signal, compared with a case where a phase is shifted through an electrical processing. In particular, in the case of the optical phase shifter, a phase shift amount is less affected whether the change in the frequency of the input light is linear or non-linear with respect to time. As a result, when a frequency-swept light is inputted, influence on the sample clock signal generated by the signal generating unit can be inhibited. In addition, in the case where the phase is shifted by the optical phase shifter, noises like those generated through an electrical processing are less likely to occur. Thus, the probability that such noises affect the sample clock signal is low.

An extent of increase in the frequency of the sample clock signal can be adjusted by the phase shift amount in the optical phase shifter. For example, the frequency of the sample clock signal can be doubled by setting the phase shift amount at 90 degrees, and when the phase shift amount is set at 45 degrees, the frequency of the sample clock signal can be quadrupled.

In the above-described invention, it is preferred that the input light incident on the optical phase shifter is a first linearly-polarized light having an inclination of +45 degrees or −45 degrees; and that the input light incident on the interference-light generating unit from the second optical path is a second linearly-polarized light having an inclination of +45 degrees or −45 degrees.

Due to the above-described configuration in which the light incident on the optical phase shifter is used as the first linearly-polarized light and the light incident on the interference-light generating unit from the second optical path is used as the second linearly-polarized light, which is independent of the first linearly-polarized light, the flexibility in configuration of the sample clock generator is increased.

In the above-described invention, it is preferred that a first linear polarizer to transmit the first linearly-polarized light is disposed on an incident side of the optical phase shifter in the first optical path; and that a second linear polarizer to transmit the second linearly-polarized light and to make the transmitted second linearly-polarized light incident on the interference-light generating unit is disposed in the second optical path.

Due to the above-described configuration in which the first linear polarizer is disposed in the first optical path and the second linear polarizer is disposed in the second optical path, a single mode fiber to guide the input light to the first optical path and the second optical path may be used, for example. The single mode fiber is less expensive and easier to handle than a polarization-maintaining fiber and the like.

In the above-described invention, it is preferred that there is further provided a polarization-maintaining fiber coupler to branch the input light emitted from the light source and linearly-polarized and to guide the first linearly-polarized light and the second linearly-polarized light to the first optical path and to the second optical path, respectively; that the first optical path at least comprises a first polarization-maintaining fiber to make the first linearly-polarized light incident on the optical phase shifter; and that the second optical path at least comprises a second polarization-maintaining fiber to make the second linearly-polarized light incident on the interference-light generating unit.

Due to the above-described configuration in which the polarization-maintaining fiber coupler, the first polarization-maintaining fiber, and the second polarization-maintaining fiber are provided, the number of components forming the sample clock generator can be reduced and optical adjustment is facilitated, compared with the case where the linear polarizers are disposed in the first optical path and the second optical path.

In the above-described invention, it is preferred that the optical phase shifter is a ¼ wavelength plate. Due to the above-described configuration in which the ¼ wavelength plate is used as the optical phase shifter, the frequency of the sample clock signal can be doubled by setting the phase shift amount at 90 degrees. In addition, the phase shift amount by the ¼ wavelength plate is less affected by the frequency of the input light. Thus, the frequency of the sample clock signal becomes less affected by the frequency of the input light.

In the above-described invention, it is preferred that there are provided a first splitting unit on which a first interference light for sample clock is made incident from among the interference lights for sample clock emitted in two different directions from the interference-light generating unit, and that splits the first interference light for sample clock into a first one split light and a first the other split light, which have different phases from each other; and a second splitting unit on which a second interference light for sample clock is made incident, and that splits the second interference light for sample clock into a second one split light and the second the other split light, which have different phases from each other; that the one light receiving unit is a balanced photodetector on which the first one split light split by the first splitting unit and the second one split light split by the second splitting unit are made incident; and that the other light receiving unit is a balanced photodetector on which the first the other split light split by the first splitting unit and the second the other split light split by the second splitting unit are made incident.

By using the first interference light for sample clock and the second interference light for sample clock as described above, the proportion of the input light to be used when generating the sample clock signal (i.e., use efficiency) is increased. It is possible to improve an SN ratio, which is a ratio between components contributing to generation of the sample clock signal and the other components, compared with the case where only either the first or the second interference light for sample clock is used.

Furthermore, the first and second interference lights for sample clock generated by the interference-light generating unit and emitted in two different directions are different in phase by 180 degrees from each other. The first interference light for sample clock and the second interference light for sample clock, which have different phases from each other, are made incident on the first splitting unit and the second splitting unit, respectively. As a result, the first one split light split by the first splitting unit and the second one split light split by the second splitting unit are different in phase by 180 degrees from each other, and the first the other split light and the second the other split light are different in phase by 180 degrees from each other. The first one split light and the second one split light, which are different in phase by 180 degrees from each other, are made incident on the one light receiving unit, which is a balanced photodetector, and the first the other split light and the second the other split light, which are also different in phase by 180 degrees from each other, are made incident on the other light receiving unit, which is a balanced photodetector. That is, a differential detection based on the split lights different in phase by 180 degrees from each other is enabled, and a contrast in interference fringes (fringes) can thereby be increased. Besides, noises (common noises) contained in common in the first one split light and the second one split light received by the one light receiving unit and/or noises contained in common in the first the other split light and the second the other split light received by the other light receiving unit are cancelled.

In the above-described invention, it is further preferred that the interference-light generating unit is a beam splitter to at least combine the input light guided through the first optical path and phase-shifted and the input light guided through the second optical path, to thereby generate the interference light for sample clock; that the first splitting unit is a first polarization beam splitter to at least split the first interference light for sample clock into a first one linearly-polarized light and a first the other linearly-polarized light, which are perpendicular to each other; that the second splitting unit is a second polarization beam splitter to at least split the second interference light for sample clock into a second one linearly-polarized light and a second the other linearly-polarized light, which are perpendicular to each other; that the one light receiving unit is a balanced photodetector on which the first one linearly-polarized light split by the first polarization beam splitter and the second one linearly-polarized light split by the second polarization beam splitter are made incident as the first one split light split by the first splitting unit and the second one split light split by the second splitting unit, respectively; and that the other light receiving unit is a balanced photodetector on which the first the other linearly-polarized light split by the first polarization beam splitter and the second the other linearly-polarized light split by the second polarization beam splitter are made incident as the first the other split light split by the first splitting unit and the second the other split light split by the second splitting unit, respectively.

In the above-described invention, it is preferred that the one light receiving unit on which the one split light is made incident and the other light receiving unit on which the other split light is made incident are each a balanced photodetector; and that the input light emitted from the light source is also made incident on the one light receiving unit and the other light receiving unit.

Due to the above-described configuration in which the input light emitted from the light source and the one split light are made incident on the balanced photodetector, which is the one light receiving unit, and a difference between the both lights is measured, it becomes easier to eliminate noises (common noises) contained in common in the input light and the one split light from the signal outputted from the one light receiving unit. Similarly, due to the configuration in which the input light and the other split light are made incident on the balanced photodetector, which is the other light receiving unit, and a difference between the both lights is measured, it becomes easier to eliminate noises contained in common in the input light and the other split light from the signal outputted from the other light receiving unit.

As described above, due to the configuration in which the input lights and the split lights are made incident on the one and the other light receiving units, which are balanced photodetectors, it is possible to reduce the above-described noises contained in common from the signals outputted from the one and the other light receiving units, with a simpler configuration than that in which two splitting units are employed.

In the above-described invention, it is preferred that the first optical path and the second optical path respectively have a first reflection unit and a second reflection unit provided therein that reflect the guided lights immediately; that the first optical path and the second optical path are separated on a side from the interference-light generating unit to the first reflection unit and the second reflection unit, whereas overlap with each other on a side of the light source, the one light receiving unit, and the other light receiving unit; that the splitting unit is disposed on a part in which the first optical path and the second optical path overlap each other; that a light transmitted through the splitting unit in the input light emitted from the light source is made incident on the interference-light generating unit; that a ⅛ wavelength plate, which is the optical phase shifter, is disposed between the first reflection unit to reflect a light transmitted through the interference-light generating unit and the interference-light generating unit; that the ¼ wavelength plate is disposed between the second reflection unit to reflect a light reflected by the interference-light generating unit and the interference-light generating unit; that the one light receiving unit at least receives at least the one linearly-polarized light obtained by splitting, by the splitting unit, the interference light for sample clock generated by the interference-light generating unit by combining the lights reflected by the first reflection unit and the second reflection unit; and that the other light receiving unit at least receives the other linearly-polarized light obtained by splitting, by the splitting unit, the interference light for sample clock generated by the interference-light generating unit by combining the lights reflected by the first reflection unit and the second reflection unit. Due to this configuration, the interference optical system can be structured as a Michelson interferometer.

In the above-described invention, it is preferred that the interference-light generating unit is a beam splitter to at least combine the input light guided through the first optical path and phase-shifted and the input light guided through the second optical path, to thereby generate the interference light for sample clock; that the splitting unit is a polarization beam splitter to at least split the interference light for sample clock into one linearly-polarized light and the other linearly-polarized light, which are perpendicular to each other; that the one light receiving unit receives the one linearly-polarized light as the one split light; and that the other light receiving unit receives the other linearly-polarized light as the other split light.

An optical tomographic imaging apparatus of the present invention includes a light source to emit a frequency-swept input light; a measurement optical system to radiate an input light branched from the emitted input light on a specimen, and also to guide a reflected light reflected from the specimen; a reference optical system that uses the other branched light as a reference light; a light receiving unit to receive a measurement interference light generated from the reflected light guided from the measurement optical system and the reference light from the reference optical system, and to output a measurement interference signal; the above-described sample clock generator of the present invention; and a signal processing unit to Fourier-analyze the measurement interference signal sampled based on the sample clock signal generated by the signal generating unit, and to acquire a tomographic image of the specimen through arithmetic processing.

According to the optical tomographic imaging apparatus of the present invention, since the above-described sample clock generator of the present invention is provided therein, the frequency of the sample clock signal defining a sampling period for acquiring the tomographic image of the specimen can be multiplied.

According to the sample clock generator for an optical tomographic imaging apparatus and the optical tomographic imaging apparatus of the present invention, an effect is exerted that the frequency of the sample clock signal can be multiplied while inhibiting the influence of the frequency of the input light, by shifting the phase of the input light guided through the first optical path with the optical phase shifter.

BRIEF DESCRIPTION OF THE DRAWINGS

The present invention will now be described by way of example with reference to the accompanying drawings, in which.

DETAILED DESCRIPTION OF THE PREFERRED EMBODIMENTS

[First Embodiment]

An explanation will be given below about an SS-OCT of a first embodiment of the present invention with reference to FIGS. 1 to 4A-4C. In the present embodiment, an optical tomographic imaging apparatus of the present invention is applied to an SS-OCT 1, and a sample clock generator for an optical tomographic imaging apparatus of the present invention is applied to a sample clock generator 100 including a Mach-Zehnder interferometer (hereinafter also referred to as a "k-clock generator 100"). The explanation will be given accordingly. The SS-OCT 1 of the present embodiment is suitably used for photographing a tomographic image of a sample (specimen) 60 in ophthalmic care, for example.

Figure 1:
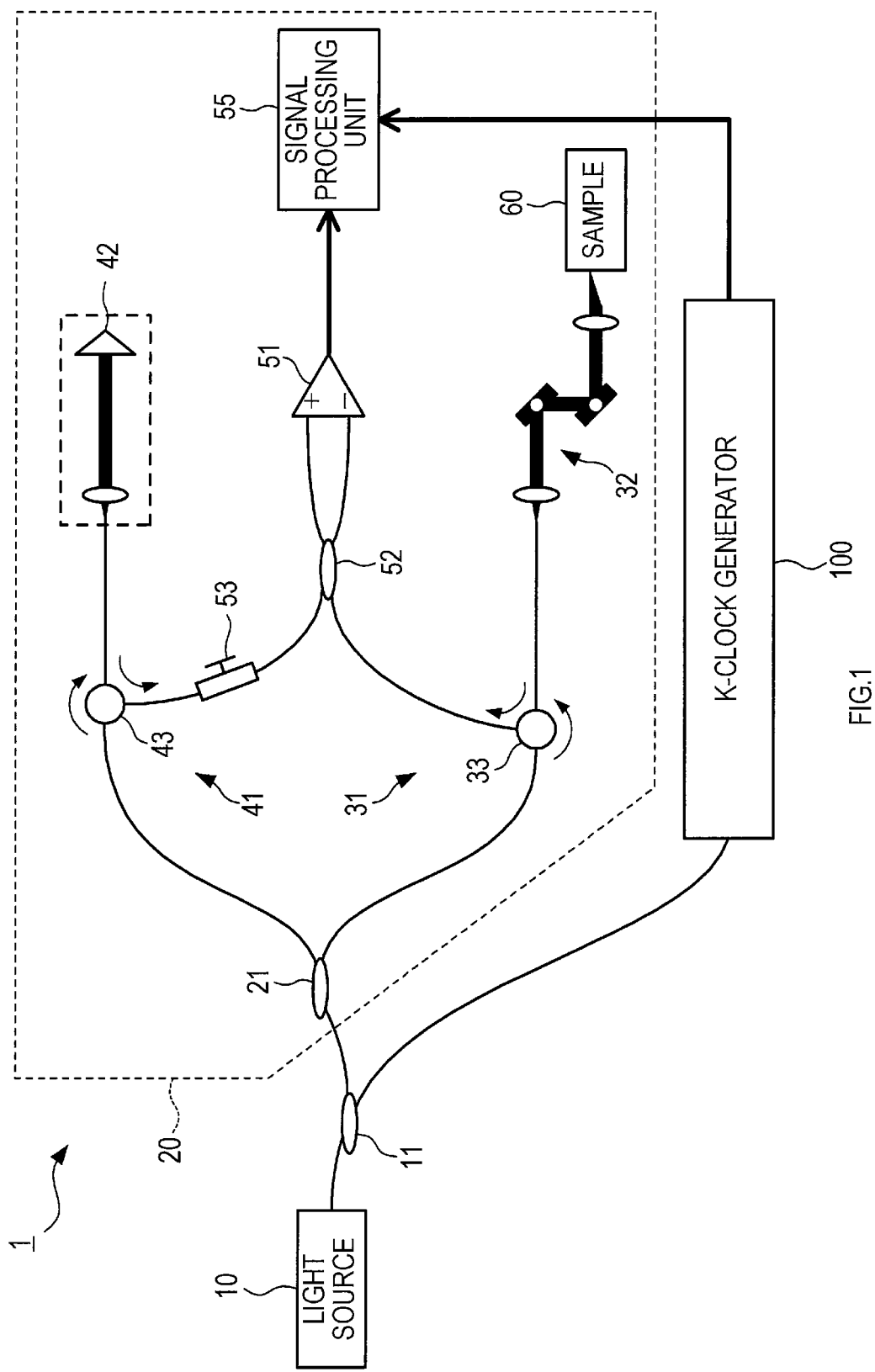
FIG. 1 is a schematic diagram explaining a configuration of an SS-OCT according to a first embodiment of the present invention.

As shown in FIG. 1, the SS-OCT 1 mainly includes a light source 10 to emit a frequency-swept input light, an OCT interference system 20 used for photographing the tomographic image of the sample 60, and the k-clock generator 100 to generate a sample clock signal (hereinafter also referred to as a "k-clock signal") that defines a sampling period for acquiring the tomographic image.

An input light emitted from the light source 10 is guided by an optical fiber such as a single mode fiber, for example, and is used for photographing the tomographic image of the sample 60, as well as for generating the sample clock signal. There is provided, between the light source 10 and the OCT interference system 20 and the k-clock generator 100, an SMFC (single mode fiber coupler) 11 to branch the emitted input light. The input light is branched by the SMFC 11 toward the OCT interference system 20 and toward the k-clock generator 100.

A method to be used for sweeping a frequency of the input light in the light source 10 may be known one, and is not limited in particular. When the frequency is swept, the frequency may increase/decrease linearly or may increase/decrease non-linearly, with respect to time.

The OCT interference system 20 mainly includes an SMFC 21 to further branch the branched input light, a measurement optical system 31 to measure the sample 60 using one of the further branched input lights, a reference optical system 41 that outputs the other of the further branched input lights as a reference light, a light receiving unit 51 to receive a measurement interference light configured with a light reflected from the sample 60 and the reference light and to output a measurement interference signal, and a signal processing unit 55 to acquire the tomographic image of the sample 60 through arithmetic processing based on the measurement interference signal.

One of the input lights branched by the SMFC 11 is made incident on the SMFC 21. The SMFC 21 further branch the incident input light into two; one is guided to the measurement optical system 31 and the other is guided to the reference optical system 41.

The measurement optical system 31 mainly includes an irradiation optical system 32 that irradiates the sample 60 with the input light and on which the light reflected from the sample 60 is made incident, and a measurement-side circulator 33 to guide the input light to the irradiation optical system 32 and to guide the reflected light to the light receiving unit 51.

The irradiation optical system 32 is an optical system to irradiate the sample 60 with the input light and to guide the light reflected from the sample 60. The irradiation optical system 32 is configured with a combination of optical elements such as a lens, a reflecting mirror, and a galvanometer mirror capable of scanning the input light in a vertical direction with respect to a depth direction of the sample 60. However, the irradiation optical system 32 is not limited in particular in terms of configuration.

The measurement-side circulator 33 is an optical element disposed among the SMFC 21, the irradiation optical system 32, and the light receiving unit 51. By the measurement-side circulator 33, the input light guided from the SMFC 21 is guided to the irradiation optical system 32, and the reflected light guided from the irradiation optical system 32 is guided to the light receiving unit 51.

The reference optical system 41 mainly includes a reference unit 42 to convert the input light into the reference light, and a reference-side circulator 43 to guide the input light to the reference unit 42 and to guide the reference light to the light receiving unit 51. In the present embodiment, the reference unit 42 is a prism to emit the incident input light as the reference light. The reference unit 42 is designed to be movable in order to match an optical path length of the measurement optical system 31 with an optical path length of the reference optical system 41 prior to measurement of the sample 60. A position of the reference unit 42 is fixed during the measurement of the sample 60.

The reference-side circulator 43 is an optical element disposed among the SMFC 21, the reference unit 42, and the light receiving unit 51. By the reference-side circulator 43, the input light guided from the SMFC 21 is guided to the reference unit 42, and the reference light guided from the reference unit 42 is guided to the light receiving unit 51.

The light receiving unit 51 is a photodetector to receive the measurement interference light generated from the reflected light guided from the measurement optical system 31 and the reference light guided from the reference optical system 41. In the present embodiment, a balanced photodetector is used as the light receiving unit 51. An SMFC 52 is disposed among the measurement optical system 31, the reference optical system 41, and the light receiving unit 51. A polarization controller 53, which is a polarization control unit, is disposed between the reference optical system 41 and the SMFC 52.

The SMFC 52 is designed to combine the reflected light guided from the measurement optical system 31 and the reference light guided from the reference optical system 41 to thereby generate the measurement interference light. Besides, the SMFC 52 is designed to branch the generated measurement interference light into two measurement interference lights, which are different in phase by 180 degrees from each other, and to guide the branched measurement interference lights to the light receiving unit 51.

The polarization controller 53 is an element to control polarization of the reference light guided from the reference optical system 41 to the SMFC 52. A polarization controller of a known type, such as of in-line type or of paddle type, may be used as the polarization controller 53, which is not limited in particular.

The signal processing unit 55 is designed to acquire the tomographic image of the sample 60 through arithmetic processing based on the measurement interference signal outputted from the light receiving unit 51, and the acquired tomographic image is displayed on a display (not shown). The processing to be performed by the signal processing unit 55 may be known one, and is not limited in particular.

Next, an explanation will be given about the k-clock generator 100, which characterizes the present embodiment, with reference to FIG. 2. As described above, the k-clock generator 100 is designed to generate the k-clock signal that defines a sampling period in the SS-OCT 1. In the present embodiment, an explanation will be given about an example of the k-clock generator 100 including the Mach-Zehnder interferometer.

Figure 2:
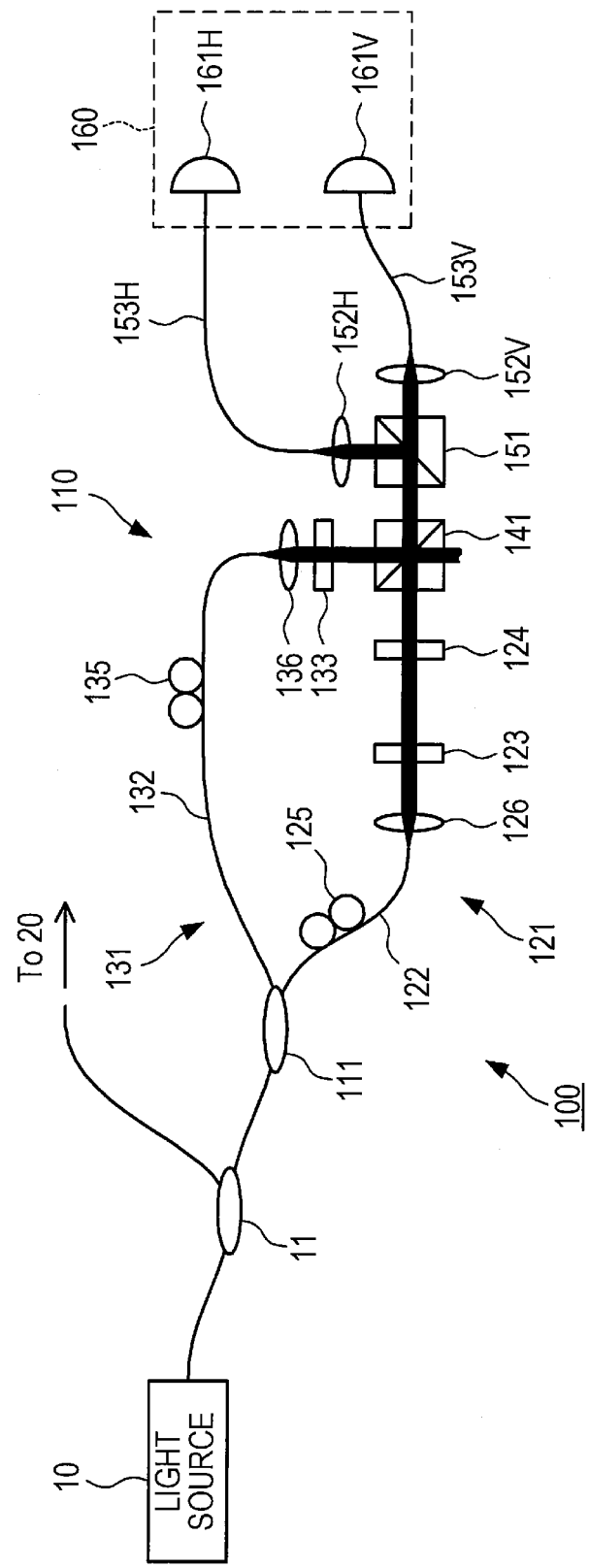
FIG. 2 is a schematic diagram explaining a configuration of a k-clock generator in FIG. 1.

As shown in FIG. 2, the k-clock generator 100 mainly includes an interference optical system 110 to generate an interference light for sample clock, and an operation unit 160 to generate the sample clock signal.

The interference optical system 110 mainly includes an SMFC 111, a first optical path 121 mainly configured with a first optical fiber 122, a first linear polarizer 123, and a ¼ wavelength plate (optical phase shifter) 124, a second optical path 131 mainly configured with a second optical fiber 132 and a second linear polarizer 133, a beam splitter (interference-light generating unit) 141, and a polarization beam splitter (splitting unit) 151.

The SMFC 111 is designed to further branch the input light branched by the SMFC 11 to the first optical path 121 and the second optical path 131. The further branched input lights are each guided to the first optical fiber 122 in the first optical path 121 and to the second optical fiber 132 in the second optical path 131. The SMFC 11, the SMFC 21, the SMFC 52, and the SMFC 111 to be used each may be an SMFC having a known configuration and is not limited in particular in terms of configuration.

The first optical fiber 122 is an optical element forming the first optical path 121 together with the first linear polarizer 123 and the ¼ wavelength plate 124. In the present embodiment, an explanation will be given about an example of the first optical fiber 122 configured with a single mode fiber.

The first optical fiber 122 has a first polarization controller 125 disposed therein that controls polarization of the guided input light. Such control of polarization of the input light by the first polarization controller 125 enables increase in the proportion of the input light to be transmitted through the first linear polarizer 123, which is to be described later.

There is disposed, between the first optical fiber 122 and the first linear polarizer 123, a first lens 126 to guide the input light emitted from the first optical fiber 122 to the first linear polarizer 123. The first lens 126 also plays a role of, for example, making the input light, which has been emitted from the first optical fiber 122 and diffused, incident on the first linear polarizer 123 and so on as a parallel light.

The first linear polarizer 123 is an optical element to transmit only a linearly-polarized light having an inclination of 45 degrees in the input light guided by the first optical fiber 122. The ¼ wavelength plate 124 is designed to shift a phase of the linearly-polarized light transmitted through the first linear polarizer 123. Specifically, the ¼ wavelength plate 124 is an optical element to delay the phase of the linearly-polarized light by a ¼ wavelength (90 degrees).

The second optical fiber 132 is an optical element forming the second optical path 131 together with the second linear polarizer 133. In the present embodiment, an explanation will be given about an example of the second optical fiber 132 configured with a single mode fiber, similarly to the first optical fiber 122.

The second optical fiber 132 has a second polarization controller 135 disposed therein that controls polarization of the guided input light. The second polarization controller 135 enables increase in the proportion of the input light to be transmitted through the second linear polarizer 133, similarly to the first polarization controller 125.

There is disposed, between the second optical fiber 132 and the second linear polarizer 133, a second lens 136 to guide the input light emitted from the second optical fiber 132 to the second linear polarizer 133. The second lens 136 plays a role similar to that of the first lens 126.

The second linear polarizer 133 is an optical element to transmit only a linearly-polarized light having an inclination of 45 degrees in the input light guided by the second optical fiber 132. The first linear polarizer 123, the second linear polarizer 133, and the ¼ wavelength plate 124 to be used each may be a known optical element and is not limited in particular in terms of form as an optical element.

The beam splitter 141 is an optical element to combine the light guided through the first optical path 121 and the light guided through the second optical path 131 to thereby generate an interference light for sample clock. Thus, the beam splitter 141 is disposed in a position at a light emitting side of the ¼ wavelength plate 124 in the first optical path 121 and also at a light emitting side of the second linear polarizer 133 in the second optical path 131.

The polarization beam splitter 151 is an optical element to split the interference light for sample clock generated by the beam splitter 141 into a vertically-polarized light (one split light, one linearly-polarized light) and a horizontally-polarized light (the other split light, the other linearly-polarized light), which are mutually-perpendicular linearly-polarized lights. It is to be noted that, although there exist a plurality of different terms for "vertically-polarized light" and "horizontally-polarized light" in the fields of electrical engineering, optics, and so on, these represent the respective same polarized lights despite the difference in terms.

The polarization beam splitter 151 is disposed in a position on which one of the two interference lights for sample clock emitted from the beam splitter 141 is made incident. The beam splitter 141 and the polarization beam splitter 151 to be used each may be a known optical element and is not limited in particular in terms of form as an optical element.

Figure 3:
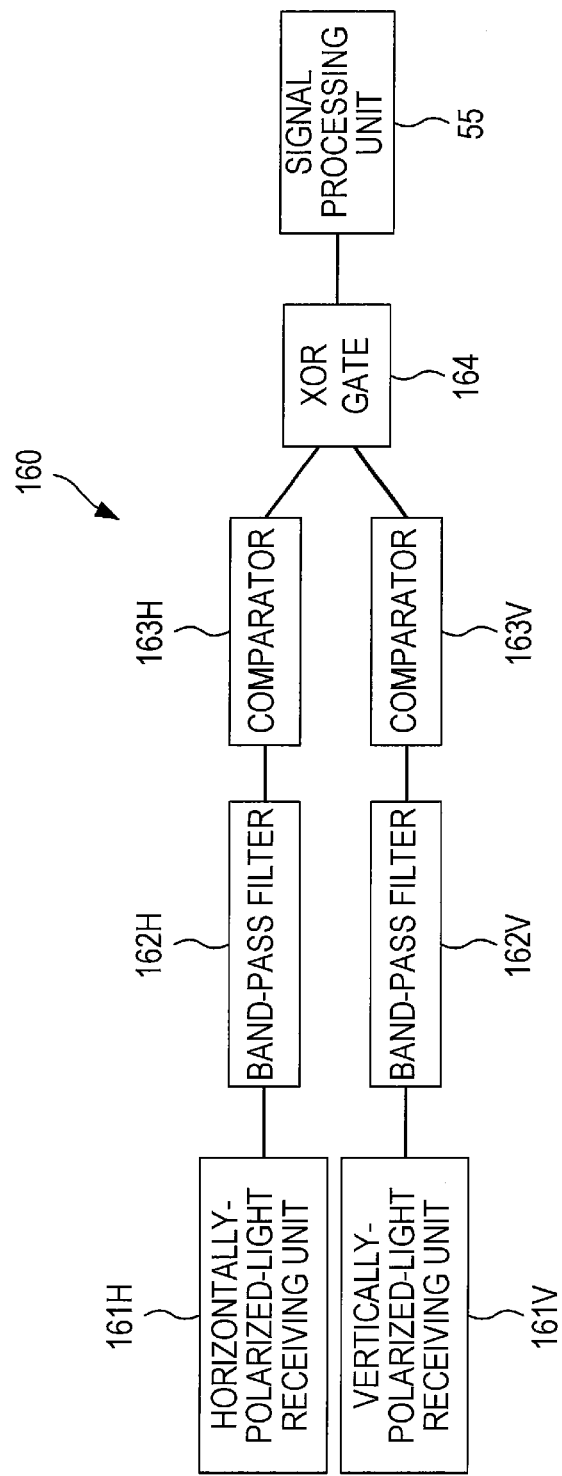
FIG. 3 is a block diagram explaining a configuration of an operation unit in FIG. 2.
Figure 4:
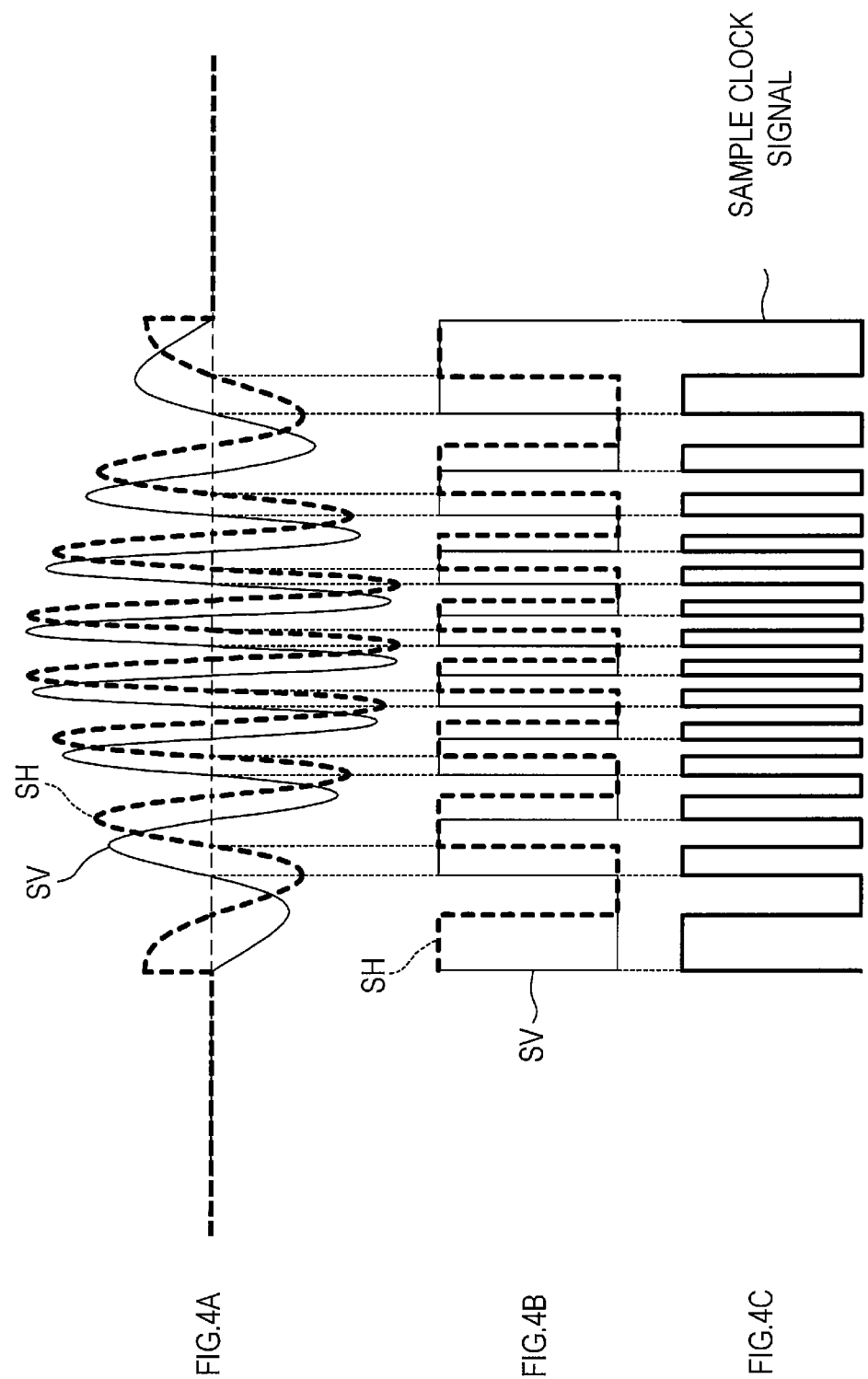
FIGS. 4A-4C are diagrams explaining correspondence among a vertical polarization signal, a horizontal polarization signal, and a sample clock signal.

As shown in FIGS. 2 and 3, the operation unit 160 mainly includes a vertically-polarized-light receiving unit (one light receiving unit) 161V, a band-pass filter 162V, and a comparator 163V, which are involved in detection of the vertically-polarized light, a horizontally-polarized-light receiving unit (the other light receiving unit) 161H, a band-pass filter 162H, and a comparator 163H, which are involved in detection of the horizontally-polarized light, and a XOR gate (signal generating unit) 164.

The vertically-polarized-light receiving unit 161V and the horizontally-polarized-light receiving unit 161H are sensors to respectively output a vertical polarization signal and a horizontal polarization signal based on the incident vertically-polarized light and the incident horizontally-polarized light, respectively. The vertically-polarized-light receiving unit 161V and the horizontally-polarized-light receiving unit 161H to be used each may be a known optical sensor. As shown in FIG. 2, there are provided, between the vertically-polarized-light receiving unit 161V and the polarization beam splitter 151, a lens 152V and a fiber 153V to guide the vertically-polarized light, and there are provided, between the horizontally-polarized-light receiving unit 161H and the polarization beam splitter 151, a lens 152H and a fiber 153H to guide the horizontally-polarized light.

The band-pass filter 162V and the band-pass filter 162H are filters to eliminate noises contained in the vertical polarization signal and the horizontal polarization signal, respectively, and to transmit only portions related to the vertically-polarized light and the horizontally-polarized light, respectively. The comparator 163V and the comparator 163H are designed to respectively convert the vertical polarization signal and the horizontal polarization signal, which are analog signals with noises thereof eliminated respectively by the band-pass filter 162V and the band-pass filter 162H, into digital signals.

The XOR gate 164 is designed to generate the sample clock signal based on the vertical polarization signal and the horizontal polarization signal respectively outputted from the comparator 163V and the comparator 163H, and to output the generated sample clock signal to the signal processing unit 55. Specifically, the sample clock signal is generated by performing an exclusive OR operation between the vertical polarization signal and the horizontal polarization signal. The band-pass filter 162V, the band-pass filter 162H, the comparator 163V, the comparator 163H, and the XOR gate 164 to be used may be known ones.

Next, an explanation will be given about an operation of the k-clock generator 100, which characterizes the present embodiment.

As shown in FIG. 2, the input light emitted from the light source 10 is inputted into the k-clock generator 100 through the SMFC 11. The input light is branched by the SMFC 111 into two; one is guided to the first optical path 121 and the other is guided to the second optical path 131.

The input light guided to the first optical path 121 is made incident on the first linear polarizer 123 after a polarization state thereof is controlled by the first polarization controller 125. Only a linearly-polarized light having an inclination of 45 degrees in the incident input light is transmitted through the first linear polarizer 123. The transmitted linearly-polarized light is converted into a circularly-polarized light by the ¼ wavelength plate 124.

The input light guided to the second optical path 131 is made incident on the second linear polarizer 133 after a polarization state thereof is controlled by the second polarization controller 135. Only a linearly-polarized light having an inclination of 45 degrees in the incident input light is transmitted through the second linear polarizer 133.

In the beam splitter 141, the circularly-polarized light converted by the ¼ wavelength plate 124 and the linearly-polarized light transmitted through the second linear polarizer 133 are combined to generate the interference light for sample clock. The generated interference light for sample clock is incident on the polarization beam splitter 151, and is split into the vertically-polarized light and the horizontally-polarized light.

As shown in FIGS. 3 and 4A-4C, the split vertically-polarized light is incident on the vertically-polarized-light receiving unit 161V, and the vertically-polarized-light receiving unit 161V outputs a vertical polarization signal SV, a value of which varies in an analog manner according to the brightness of the vertically-polarized light. Similarly, the horizontally-polarized light is incident on the horizontally-polarized-light receiving unit 161H, and the horizontally-polarized-light receiving unit 161H outputs a horizontal polarization signal SH, a value of which varies according to the brightness of the horizontally-polarized light.

Here, FIG. 4A shows the vertical polarization signal SV and the horizontal polarization signal SH, with the horizontal axis denoting time, and the vertical axis denoting a signal value. Since the phase has been shifted by the ¼ wavelength plate 124, there exists a phase difference of a ¼ wavelength between the vertical polarization signal SV and the horizontal polarization signal SH.

Noise components of the vertical polarization signal SV and the horizontal polarization signal SH are respectively eliminated by the band-pass filter 162V and the band-pass filter 162H. Then, the vertical polarization signal SV and the horizontal polarization signal SH are converted into digital-like signals, values of which vary in a rectangular wave shape, by the comparator 163V and the comparator 163H, respectively.

Specifically, a processing is performed in such a manner that, when the value of the signal before conversion is less than 0, the signal is converted into a signal having a relatively low value (e.g., 0), and when the value of the signal before conversion is greater than 0, the signal is converted into a signal having a relatively high value (e.g., 1). In other words, the conversion is performed in such a manner that, each time the value of the signal before conversion varies across 0, the value of the signal after conversion is varied from the high value to the low value or from the low value to the high value.

FIG. 4B shows the vertical polarization signal SV and the horizontal polarization signal SH respectively converted by the comparator 163V and the comparator 163H. Also between the vertical polarization signal SV and the converted horizontal polarization signal SH after conversion, there exists a phase difference of ¼ wavelength, similarly to those before conversion.

The vertical polarization signal SV and the horizontal polarization signal SH respectively converted by the comparator 163V and the comparator 163H are inputted into the XOR gate 164. The XOR gate 164 performs a processing of generating the sample clock signal based on the inputted vertical polarization signal SV and the inputted horizontal polarization signal SH. FIG. 4C shows the sample clock signal generated by the XOR gate 164.

According to the thus-configured k-clock generator 100, a frequency of the sample clock signal generated by the XOR gate 164 can be multiplied (doubled, in the present embodiment) while inhibiting an influence of a frequency of the input light on the frequency of the sample clock signal by shifting the phase of the input light guided through the first optical path 121 with the ¼ wavelength plate 124.

The phase of the input light shifted by the ¼ wavelength plate 124 is less affected by the frequency of the input light, which is an input signal, compared with a case in which a phase is shifted through an electrical processing. In particular, in the case of the ¼ wavelength plate 124, a phase shift amount is less affected whether the change in the frequency of the input light is linear or non-linear with respect to time. As a result, when a frequency-swept light is inputted, influence on the sample clock signal generated by the XOR gate 164 can be inhibited. In addition, in the case where the phase is shifted by the ¼ wavelength plate 124, noises like those generated through an electrical processing are less likely to occur. Thus, the probability that such noises affect the sample clock signal is low.

Due to the configuration in which the first linear polarizer 123 is disposed in the first optical path 121 and the second linear polarizer 133 is disposed in the second optical path 131, a single mode fiber to guide the input light to the first optical path 121 and the second optical path 131 may be used, for example. The single mode fiber is less expensive and easier to handle than a polarization-maintaining fiber and the like. Furthermore, by using the ¼ wavelength plate 124 as an optical phase shifter, the frequency of the sample clock signal can be doubled by setting the phase shift amount at 90 degrees.

An extent of increase in the frequency of the sample clock signal as described above can be adjusted by the phase shift amount of the light in the first optical path 121. For example, as in the above-described embodiment, the frequency of the sample clock signal can be doubled by setting the phase shift amount at 90 degrees using the ¼ wavelength plate 124. Furthermore, when the phase shift amount is set at 45 degrees using a ⅛ wavelength plate, the frequency of the sample clock signal can be quadrupled.

The linearly-polarized light transmitted through the first linear polarizer 123 and the linearly-polarized light transmitted through the second linear polarizer 133 are independent of each other. Therefore, the inclinations of the linearly-polarized lights may be both 45 degrees (the same as each other) as in the above-described embodiment, may be different from each other (one is +45 degrees and the other is −45 degrees), or may be both −45 degrees (the same as each other). Accordingly, more choices are available as to the first linear polarizer 123 and the second linear polarizer 133 in the k-clock generator 100, and the flexibility in configuration thereof is increased.

[Second Embodiment]

Next, an explanation will be given about an SS-OCT of a second embodiment of the present invention with reference to FIG. 5. Although a basic configuration of the SS-OCT of the present embodiment is similar to that of the first embodiment, a configuration of a k-clock generator is different from that of the first embodiment. Thus, in the present embodiment, an explanation will be given only about the k-clock generator with reference to FIG. 5, and an explanation of the other components and so on is omitted.

Figure 5:
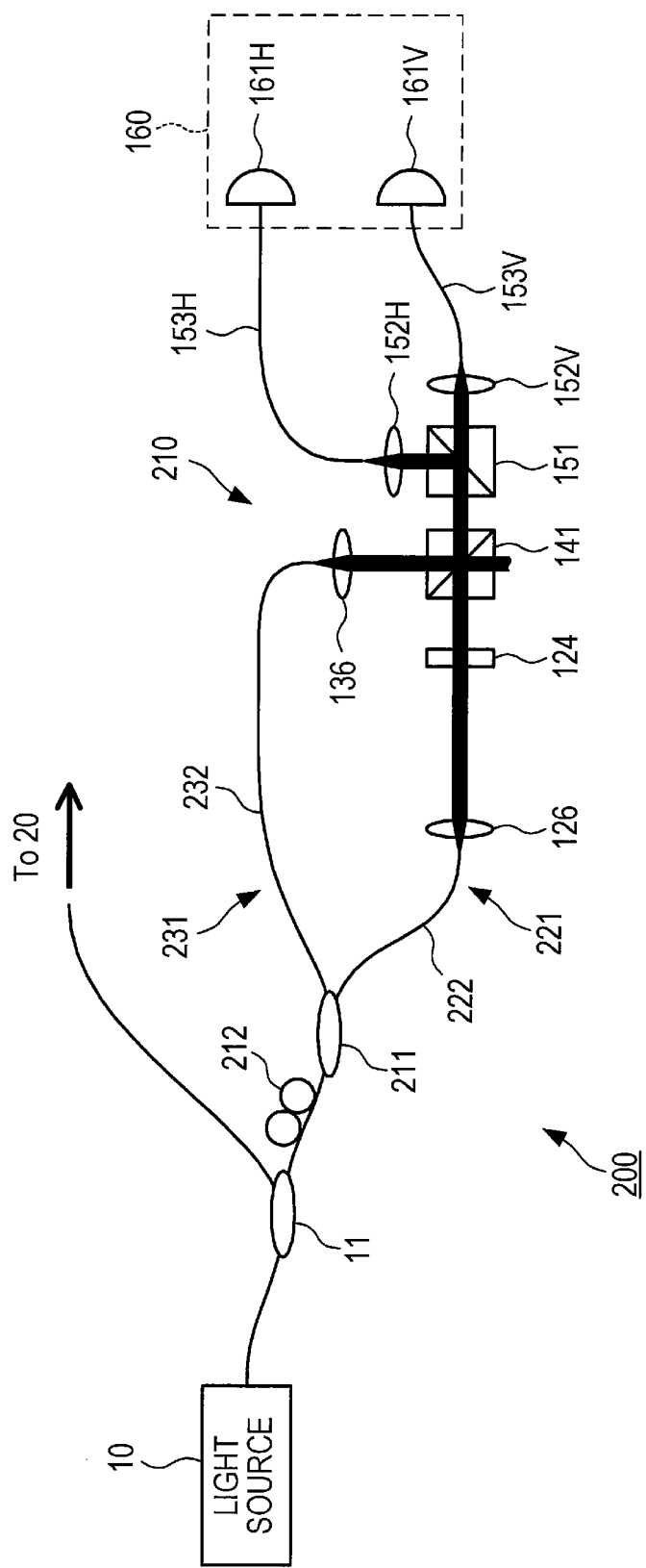
FIG. 5 is a schematic diagram explaining a configuration of a k-clock generator according to a second embodiment of the present invention.

As shown in FIG. 5, a k-clock generator (sample clock generator) 200 of the present embodiment mainly includes an interference optical system 210 to generate an interference light for sample clock and the operation unit 160 to generate a sample clock signal.

The interference optical system 210 mainly includes a PMFC (polarization-maintaining fiber coupler) 211, a first optical path 221 mainly configured with a first optical fiber (first polarization-maintaining fiber) 222 and the ¼ wavelength plate 124, a second optical path 231 mainly configured with a second optical fiber (second polarization-maintaining fiber) 232, the beam splitter 141, and the polarization beam splitter 151.

The PMFC 211 is designed to further branch the input light branched by the SMFC 11 to the first optical path 221 and the second optical path 231, and also to guide the branched input lights, as linearly-polarized lights, to the first optical path 221 and the second optical path 231. The branched linearly-polarized lights are guided to the first optical fiber 222 in the first optical path 221 and to the second optical fiber 232 in the second optical path 231. The PMFC 211 to be used may be a PMFC having a known configuration, and is not limited in particular in terms of configuration.

There is disposed, between the SMFC 11 and the PMFC 211, a polarization controller 212 to control polarization of the guided input light. Such control of polarization of the input light by the polarization controller 212 enables increase in the proportion of the linearly-polarized light to be guided from the PMFC 211 to the first optical path 221 and to the second optical path 231.

The first optical fiber 222 is an optical element forming the first optical path 221 together with the ¼ wavelength plate 124. The first optical fiber 222 is disposed so as to emit the linearly-polarized light having an inclination of 45 degrees toward the ¼ wavelength plate 124. The second optical fiber 232 is an optical element forming the second optical path 231, and is disposed so as to emit the linearly-polarized light having an inclination of 45 degrees toward the beam splitter 141.

In the present embodiment, an explanation will be given about an example of the first optical fiber 222 and the second optical fiber 232 each configured with the polarization-maintaining fiber that leads a light while maintaining a linear polarization state.

Next, an explanation will be given about an operation of the k-clock generator 200, which characterizes the present embodiment.

As shown in FIG. 5, the input light emitted from the light source 10 is inputted into the k-clock generator 200 through the SMFC 11. The input light is branched by the PMFC 211 into two; one is guided to the first optical path 221 and the other is guided to the second optical path 231.

The linearly-polarized light guided to the first optical path 221 is emitted to the ¼ wavelength plate 124 as a linearly-polarized light having an inclination of 45 degrees, and is converted into a circularly-polarized light by the ¼ wavelength plate 124. The linearly-polarized light guided to the second optical path 231 is emitted toward the beam splitter 141 as a linearly-polarized light having an inclination of 45 degrees.

In the beam splitter 141, the circularly-polarized light converted by the ¼ wavelength plate 124 and the linearly-polarized light guided through the second optical path 231 are combined to generate an interference light for sample clock. The generated interference light for sample clock is incident on the polarization beam splitter 151, and is split into a vertically-polarized light and a horizontally-polarized light. Since an operation hereafter is similar to that in the first embodiment, an explanation is omitted here.

According to the thus-configured k-clock generator 200, the number of components forming the k-clock generator 200 can be reduced compared with the case as in the first embodiment, in which the linear polarizers are disposed in the first optical path 121 and the second optical path 131, by providing the k-clock generator 200 with the PMFC 211, the first optical fiber 222, and the second optical fiber 232.

[Third Embodiment]

Next, an explanation will be given about an SS-OCT of a third embodiment of the present invention with reference to FIG. 6. Although a basic configuration of the SS-OCT of the present embodiment is similar to that of the second embodiment, a configuration of a k-clock generator is different from that of the second embodiment. Thus, in the present embodiment, an explanation will be given only about the k-clock generator with reference to FIG. 6, and an explanation of the other components and so on is omitted.

Figure 6:
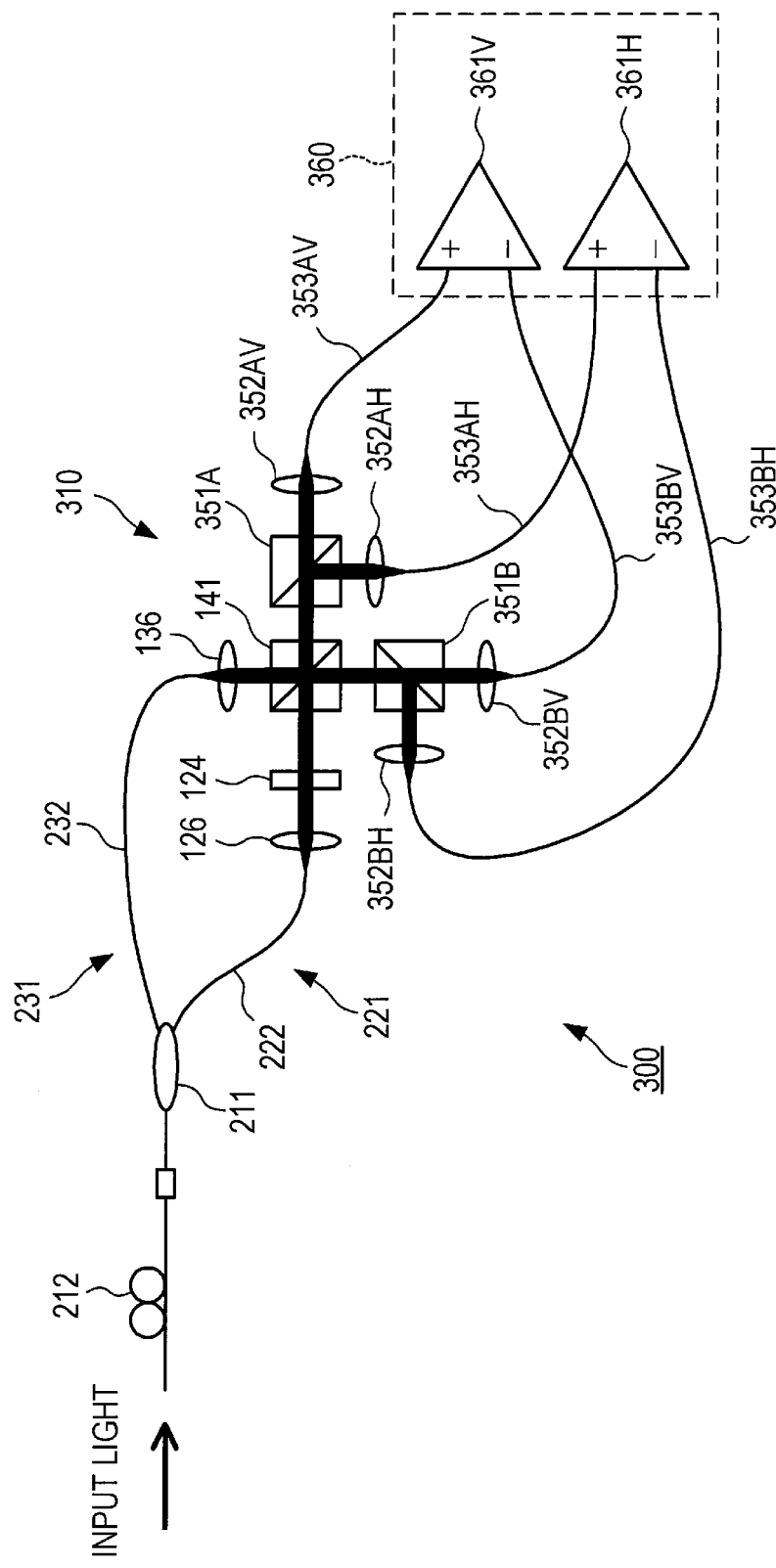
FIG. 6 is a schematic diagram explaining a configuration of a k-clock generator according to a third embodiment of the present invention.

As shown in FIG. 6, a k-clock generator (sample clock generator) 300 of the present embodiment mainly includes an interference optical system 310 to generate an interference light for sample clock and an operation unit 360 to generate a sample clock signal.

The interference optical system 310 mainly includes the PMFC 211, the first optical path 221 mainly configured with the first optical fiber 222 and the ¼ wavelength plate 124, the second optical path 231 mainly configured with the second optical fiber 232, the beam splitter 141, a first polarization beam splitter 351A, and a second polarization beam splitter 351B.

The first polarization beam splitter 351A is an optical element to split a first interference light for sample clock generated by the beam splitter 141 into a vertically-polarized light (first one linearly-polarized light) and a horizontally-polarized light (first the other linearly-polarized light), which are mutually-perpendicular linearly-polarized lights. The second polarization beam splitter 351B is an optical element to split a second interference light for sample clock generated by the beam splitter 141 to a vertically-polarized light (second one linearly-polarized light) and a horizontally-polarized light (second the other linearly-polarized light), which are mutually-perpendicular linearly-polarized lights.

The first polarization beam splitter 351A is disposed in a position on which the first interference light for sample clock, which is one of the two interference lights for sample clock emitted from the beam splitter 141, is made incident. The second polarization beam splitter 351B is disposed in a position on which the second interference light for sample clock, which is the other of the two interference lights for sample clock, is made incident. The first polarization beam splitter 351A and the second polarization beam splitter 351B to be used may be known ones.

The operation unit 360 has a configuration same as that of the operation unit 160 of the first embodiment, except for a point that a vertically-polarized-light receiving unit (one light receiving unit) 361V and a horizontally-polarized-light receiving unit (the other light receiving unit) 361H are used instead of the vertically-polarized-light receiving unit 161V and the horizontally-polarized-light receiving unit 161H.

The vertically-polarized-light receiving unit 361V is a balanced photodetector, into which the vertically-polarized lights split by the first polarization beam splitter 351A and the second polarization beam splitter 351B are inputted. The horizontally-polarized-light receiving unit 361H is a balanced photodetector, into which the horizontally-polarized lights split by the first polarization beam splitter 351A and the second polarization beam splitter 351B are inputted.

There are disposed, between the vertically-polarized-light receiving unit 361V and the first polarization beam splitter 351A, a first lens 352AV and a first fiber 353AV, which guide the vertically-polarized light. On the other hand, there are disposed, between the horizontally-polarized-light receiving unit 361H and the first polarization beam splitter 351A, a first lens 352AH and a first fiber 353AH, which guide the horizontally-polarized light.

Furthermore, there are disposed, between the vertically-polarized-light receiving unit 361V and the second polarization beam splitter 351B, a second lens 352BV and a second fiber 353BV, which guide the vertically-polarized light. On the other hand, there are disposed, between the horizontally-polarized-light receiving unit 361H and the second polarization beam splitter 351B, a second lens 352BH and a second fiber 353BH, which guide the horizontally-polarized light.

Next, an explanation will be given about an operation of the k-clock generator 300, which characterizes the present embodiment. Since an operation performed from input of the input light emitted from the light source 10 into the k-clock generator 300 till generation of the first and second interference lights for sample clock by the beam splitter 141 is similar to that in the second embodiment, an explanation is omitted here.

The first and second interference lights for sample clock generated by the beam splitter 141 are emitted in two different directions, and a phase difference of 180 degrees exists between the both interference lights. One of the interference lights for sample clock is made incident on the first polarization beam splitter 351A, and is split into the vertically-polarized light and the horizontally-polarized light. The other of the interference lights for sample clock is made incident on the second polarization beam splitter 351B, and is split into the vertically-polarized light and the horizontally-polarized light.

The vertically-polarized lights split by the first polarization beam splitter 351A and the second polarization beam splitter 351B are made incident on the vertically-polarized-light receiving unit 361V. On the other hand, the horizontally-polarized lights split by the first polarization beam splitter 351A and the second polarization beam splitter 351B are made incident on the horizontally-polarized-light receiving unit 361H. The vertically-polarized-light receiving unit 361V performs a differential detection using the two vertically-polarized lights different in incident phase by 180 degrees from each other, and outputs a vertical polarization signal SV. The horizontally-polarized-light receiving unit 361H performs a differential detection using the two horizontally-polarized lights different in incident phase by 180 degrees from each other, and outputs a horizontal polarization signal SH. Since an operation hereafter is similar to that in the first embodiment, an explanation is omitted here.

According to the thus-configured k-clock generator 300, the proportion of the input light to be used when generating the sample clock signal (i.e., use efficiency) is increased by using the two interference lights for sample clock different in phase by 180 degrees from each other. It is possible to improve an SN ratio, which is a ratio between components contributing to generation of the sample clock signal and the other components, compared with the case where only one or the other of the interference lights for sample clock is used.

In addition, since the vertically-polarized-light receiving unit 361V and the horizontally-polarized-light receiving unit 361H are balanced photodetectors, the differential detection based on the linearly-polarized lights different in phase by 180 degrees from each other is enabled as described above, and a contrast in interference fringes (fringes) can thereby be increased. Besides, it is possible to cancel noises (common noises) contained in common in the two vertically-polarized lights received by the vertically-polarized-light receiving unit 361V and/or noises contained in common in the two horizontally-polarized lights received by the horizontally-polarized-light receiving unit 361H.

[Fourth Embodiment]

Next, an explanation will be given about an SS-OCT of a fourth embodiment of the present invention with reference to FIG. 7.

Although a basic configuration of the SS-OCT of the present embodiment is similar to that of the third embodiment, a configuration of a k-clock generator is different from that of the third embodiment. Thus, in the present embodiment, an explanation will be given only about the k-clock generator with reference to FIG. 7, and an explanation of the other components and so on is omitted.

Figure 7:
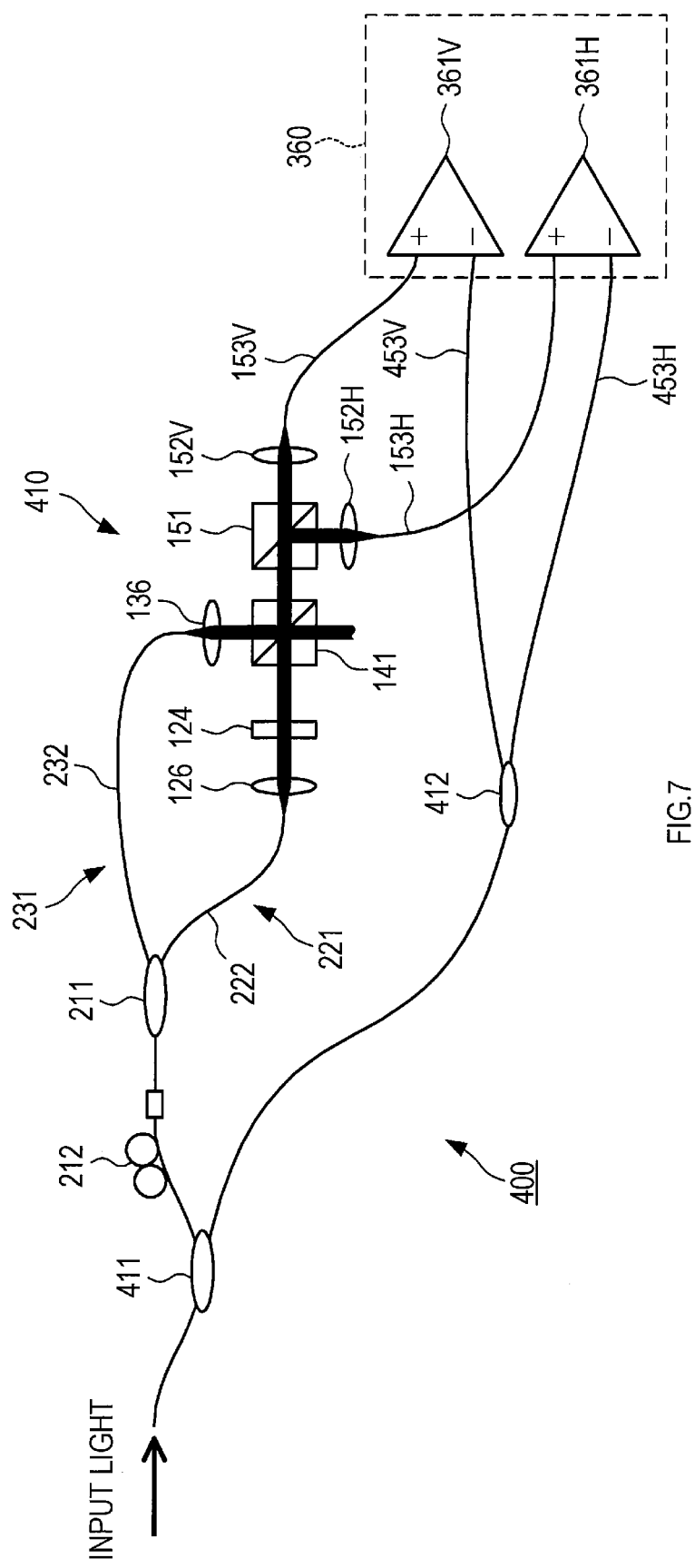
FIG. 7 is a schematic diagram explaining a configuration of a k-clock generator according to a fourth embodiment of the present invention.

As shown in FIG. 7, a k-clock generator (sample clock generator) 400 of the present embodiment mainly includes an interference optical system 410 to generate an interference light for sample clock and the operation unit 360 to generate a sample clock signal.

The interference optical system 410 mainly includes an SMFC 411, the PMFC 211, the first optical path 221 mainly configured with the first optical fiber 222 and the ¼ wavelength plate 124, the second optical path 231 mainly configured with the second optical fiber 232, the beam splitter 141, and the polarization beam splitter 151.

The SMFC 411 is designed to branch an input light emitted from the light source 10 toward the PMFC 211 and toward the vertically-polarized-light receiving unit 361V and the horizontally-polarized-light receiving unit 361H. There is disposed, between the SMFC 411 and the vertically-polarized-light receiving unit 361V and the horizontally-polarized-light receiving unit 361H, an SMFC 412 to further branch the input light. One of the input lights branched by the SMFC 412 is guided by an optical fiber 453V and made incident on the vertically-polarized-light receiving unit 361V. The other of the input lights is guided by an optical fiber 453H and made incident on the horizontally-polarized-light receiving unit 361H.

Next, an explanation will be given about an operation of the k-clock generator 400, which characterizes the present embodiment. Since an operation performed from input of the input light emitted from the light source 10 into the k-clock generator 400 till incidence of the vertically-polarized light and the horizontally-polarized light, which are split by the polarization beam splitter 151, into the vertically-polarized-light receiving unit 361V and the horizontally-polarized-light receiving unit 361H, respectively, is similar to that in the third embodiment, an explanation is omitted here.

The input light branched by the SMFC 411 and made incident on the SMFC 412 is further branched and made incident on the vertically-polarized-light receiving unit 361V and the horizontally-polarized-light receiving unit 361H through the optical fiber 453V and the optical fiber 453H, respectively. The vertically-polarized-light receiving unit 361V performs a differential detection using the incident vertically-polarized light and the incident input light, and outputs a vertical polarization signal SV. The horizontally-polarized-light receiving unit 361H performs a differential detection using the incident horizontally-polarized light and the incident input light, and outputs a horizontal polarization signal SH. Since an operation hereafter is similar to that in the first embodiment, an explanation is omitted here.

According to the thus-configured k-clock generator 400, it is possible to reduce noises (common noises) contained in common in the input light and the vertically-polarized light and/or noises contained in common in the input light and the horizontally-polarized light, by adopting a configuration in which a difference between the input light and the vertically-polarized light is detected using the vertically-polarized-light receiving unit 361V, which is a balanced photodetector, and a configuration in which a difference between the input light and the horizontally-polarized light is detected using the horizontally-polarized-light receiving unit 361H, which is also a balanced photodetector.

As described above, a configuration in which the input light and the vertically-polarized light are made incident on the vertically-polarized-light receiving unit 361V and in which the input light and the horizontally-polarized light are made incident on the horizontally-polarized-light receiving unit 361H makes it possible to reduce the above-described noises and so on contained in common and to facilitate an optical adjustment such as an optical axis alignment, with a simpler configuration than that of the third embodiment.

[Fifth Embodiment]

Next, an explanation will be given about an SS-OCT of a fifth embodiment of the present invention with reference to FIG. 8.

Although a basic configuration of the SS-OCT of the present embodiment is similar to that of the first embodiment, a configuration of a k-clock generator is different from that of the first embodiment. Thus, in the present embodiment, an explanation will be given only about the k-clock generator with reference to FIG. 8, and an explanation of the other components and so on is omitted.

In the present embodiment, an explanation will be given about an example of a k-clock generator 500 including a Michelson interferometer. As shown in FIG. 8, the k-clock generator 500 mainly includes an interference optical system 510 to generate an interference light for sample clock and the operation unit 360 to generate a sample clock signal.

The interference optical system 510 mainly includes the SMFC 111, a polarization beam splitter (splitting unit) 551, a beam splitter (interference-light generating unit) 541, a first optical path 521 configured at least with a ⅛ wavelength plate (optical phase shifter) 524 and a first mirror (first reflection unit) 525, and a second optical path 531 configured at least with a ¼ wavelength plate 534 and a second mirror (second reflection unit) 535.

The SMFC 111 is designed to further branch the input light branched by the SMFC 11 toward the polarization beam splitter 551 and toward the SMFC 412. There are disposed, between the SMFC 111 and the polarization beam splitter 551, a polarization controller 512 and a circulator 513.

The polarization controller 512 is designed to control a polarization state of the input light to be guided from the SMFC 111 to the polarization beam splitter 551. Such control of the polarization state of the input light enables increase in the proportion of the polarized light to be transmitted through the polarization beam splitter 551.

The circulator 513 is designed to guide the input light from the SMFC 111 toward the polarization beam splitter 551, and to guide the vertically-polarized light from the polarization beam splitter 551 toward the vertically-polarized-light receiving unit 361V.

The polarization beam splitter 551 is an optical element to transmit only the vertically-polarized light in the input light guided from the SMFC 111 and to emit the transmitted light to the beam splitter 541. Furthermore, the polarization beam splitter 551 is also an optical element to split the interference light for sample clock emitted from the beam splitter 541 into a vertically-polarized light and a horizontally-polarized light, which are mutually-perpendicular linearly-polarized lights.

A lens 552 and a lens 553 are respectively disposed on a side of the SMFC 111 and on a side of the horizontally-polarized-light receiving unit 361H, with respect to the polarization beam splitter 551. The lens 552 is designed to make the light guided from the SMFC 111 through an optical fiber incident on the polarization beam splitter 551 as a parallel light. The lens 552 is also designed to make the vertically-polarized light split by the polarization beam splitter 551 incident on the optical fiber. The lens 553 is designed to make the horizontally-polarized light split by the polarization beam splitter 551 incident on an optical fiber.

The beam splitter 541 is an optical element to split the vertically-polarized light guided from the polarization beam splitter 551 into two, and also to combine a circularly-polarized light emitted from the ⅛ wavelength plate 524 and a linearly-polarized light having an inclination of 45 degrees emitted from the ¼ wavelength plate 534 to thereby generate the interference light for sample clock.

The ⅛ wavelength plate 524 and the first mirror 525 are disposed adjacent to one of two faces of the beam splitter 541, from which faces the vertically-polarized lights are emitted, and the ¼ wavelength plate 534 and the second mirror 535 are disposed adjacent to the other of the two faces. The ⅛ wavelength plate 524 is an optical element to delay a phase of the incident light by ⅛ wavelength, and the ¼ wavelength plate 534 is an optical element to delay a phase of the incident light by ¼ wavelength.

The first mirror 525 is a reflecting mirror on which the light transmitted through the ⅛ wavelength plate 524 is made incident, and the reflected light is made incident on the ⅛ wavelength plate 524. A first lens 526 is further disposed between the ⅛ wavelength plate 524 and the first mirror 525.

The second mirror 535 is a reflecting mirror on which the light transmitted through the ¼ wavelength plate 534 is made incident, and the reflected light is made incident on the ¼ wavelength plate 534. A second lens 536 is further disposed between the ¼ wavelength plate 534 and the second mirror 535.

Next, an explanation will be given about an operation of the k-clock generator 500, which characterizes the present embodiment.

Figure 8:
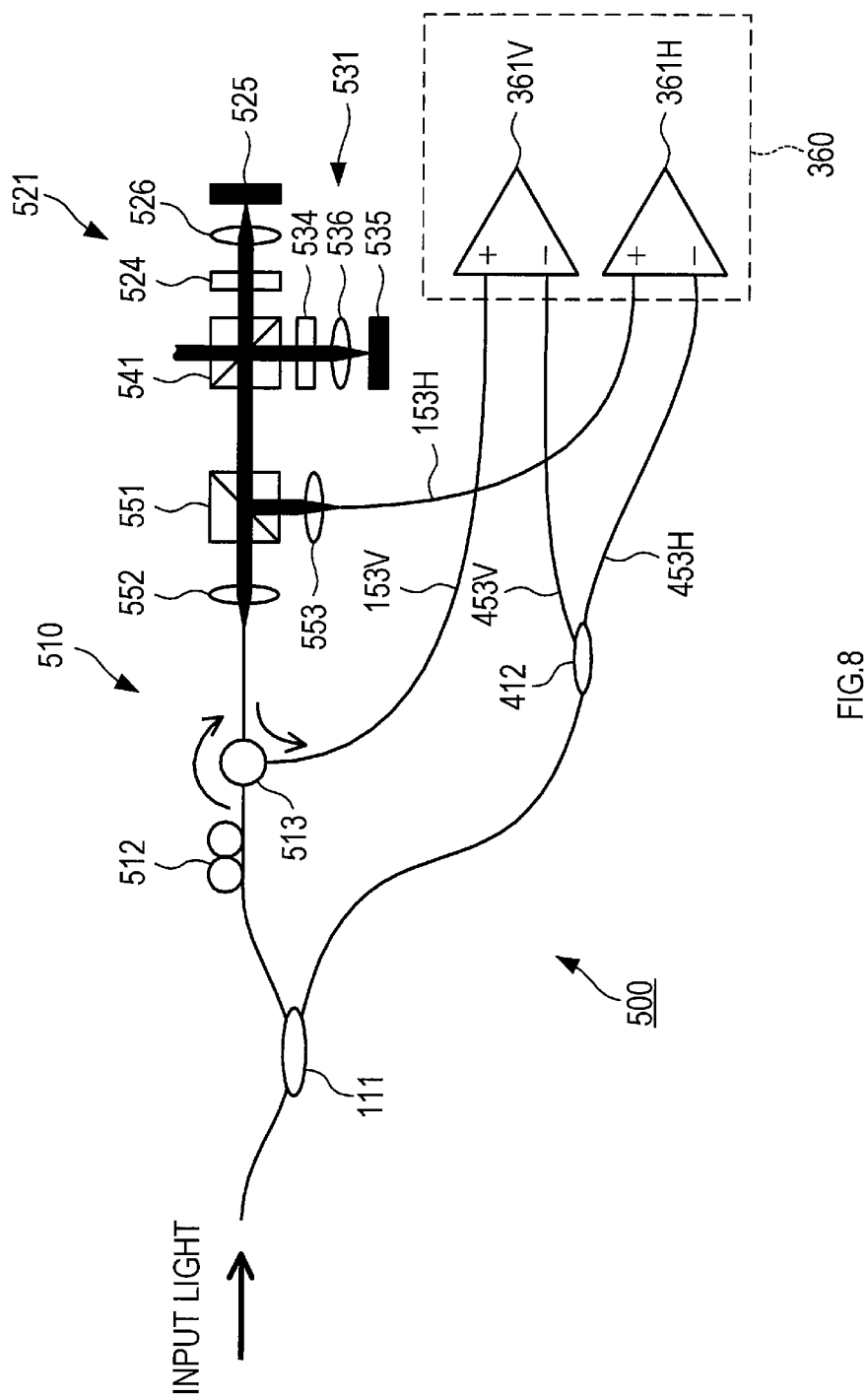
FIG. 8 is a schematic diagram explaining a configuration of a k-clock generator according to a fifth embodiment of the present invention.

As shown in FIG. 8, the input light is inputted into the SMFC 111 of the k-clock generator 500. The input light is branched by the SMFC 111 into two; one is guided toward the polarization beam splitter 551, and the other is guided toward the SMFC 412.

The input light guided toward the polarization beam splitter 551 is made incident on the polarization beam splitter 551 through the circulator 513 after a polarization state thereof is controlled by the polarization controller 512. The input light is split by the polarization beam splitter 551 into the vertically-polarized light and the horizontally-polarized light, and the vertically-polarized light is emitted toward the beam splitter 541.

The vertically-polarized light is branched by the beam splitter 541 into two; one is emitted toward the ⅛ wavelength plate 524 and the other is emitted toward the ¼ wavelength plate 534. The incident vertically-polarized light is transmitted through the ⅛ wavelength plate 524, and reflected by the first mirror 525. Then, the reflected light is transmitted through the ⅛ wavelength plate 524 again to thereby be converted into a circularly-polarized light. The incident linearly-polarized light is transmitted through the ¼ wavelength plate 534, and reflected by the second mirror 535. Then, the reflected light is transmitted through the ¼ wavelength plate 534 again to thereby be converted into a linearly-polarized light having an inclination of 45 degrees.

The circularly-polarized light converted by the ⅛ wavelength plate 524 and the linearly-polarized light having an inclination of 45 degrees converted by the ¼ wavelength plate 534 are combined by the beam splitter 541 to thereby generate the interference light for sample clock. The interference light for sample clock is incident on the polarization beam splitter 551 and is split into a vertically-polarized light and a horizontally-polarized light. The split vertically-polarized light is made incident on the vertically-polarized-light receiving unit 361V through the circulator 513. On the other hand, the split horizontally-polarized light is made incident on the horizontally-polarized-light receiving unit 361H.

The input light branched by the SMFC 111 and guided to the SMFC 412 is further branched by the SMFC 412 into two; one is made incident on the vertically-polarized-light receiving unit 361V and the other is made incident on the horizontally-polarized-light receiving unit 361H. The vertically-polarized-light receiving unit 361V performs a differential detection using the incident vertically-polarized light and the incident input light, and outputs a vertical polarization signal SV. The horizontally-polarized-light receiving unit 361H performs a differential detection using the incident horizontally-polarized light and the incident input light, and outputs a horizontal polarization signal SH. Since an operation hereafter is similar to that in the first embodiment, an explanation is omitted here.

According to the thus-configured k-clock generator 500, it is possible to configure the k-clock generator 500 including the Michelson interferometer, instead of the Mach-Zehnder interferometer as in the first embodiment to the fourth embodiment.

It is to be noted that the technical scope of the present invention is not limited to the above-described embodiments, and various modifications can be made within the scope not departing from the spirit of the present invention. For example, application of the present invention is not limited in particular, and the present invention may be applied not only to the above-described embodiments but also to appropriate combinations thereof.

EXPLANATION OF REFERENCE NUMERALS

1 . . . SS-OCT (optical tomographic imaging apparatus), 10 . . . light source, 31 . . . measurement optical system, 41 . . . reference optical system, 51 . . . light receiving unit, 55 . . . signal processing unit, 60 . . . sample (specimen), 100, 200, 300, 400, 500 . . . k-clock generator (sample clock generator), 110, 210, 310, 410, 510 . . . interference optical system, 121, 221, 521 . . . first optical path, 123 . . . first linear polarizer, 124 . . . ¼ wavelength plate (optical phase shifter), 131, 231, 531 . . . second optical path, 133 . . . second linear polarizer, 141, 541 . . . beam splitter (interference-light generating unit), 151, 551 . . . polarization beam splitter (splitting unit), 160, 360 . . . operation unit, 161V, 361V . . . vertically-polarized-light receiving unit (one light receiving unit), 161H, 361H . . . horizontally-polarized-light receiving unit (the other light receiving unit), 164 . . .

XOR gate (signal generating unit), 211 . . . PMFC (polarization-maintaining fiber coupler), 222 . . . first optical fiber (first polarization-maintaining fiber), 232 . . . second optical fiber (second polarization-maintaining fiber), 351A . . . first polarization beam splitter, 351B . . . second polarization beam splitter, 524 . . . ⅛ wavelength plate (optical phase shifter), 525 . . . first mirror (first reflection unit), 534 . . . ¼ wavelength plate, 535 . . . second mirror (second reflection unit)

What is claimed is:

1. A sample clock generator for an optical tomographic imaging apparatus configured to receive a frequency-swept input light emitted from a light source and to generate a sample clock signal, the sample clock generator comprising:
   an interference optical system comprising:
      a first optical path through which part of the input light is guided;
      a second optical path through which other part of the input light is guided;
      an optical phase shifter to shift a phase of the input light guided through the first optical path;
      an interference-light generator to combine the input light guided through the first optical path and phase-shifted and the input light guided through the second optical path, to thereby generate an interference light for sample clock; and
      a splitter to split the interference light for sample clock into a first split light and a second split light having different phases; and
   an operator at least comprising:
      a first light receiver to at least receive the first split light;
      a second light receiver to at least receive the second split light; and
      a signal generator to generate the sample clock signal based on signals outputted from the first light receiver and the second light receiver.

2. The sample clock generator for an optical tomographic imaging apparatus according to claim 1,
   wherein the input light incident on the optical phase shifter is a first linearly-polarized light having an inclination of +45 degrees or −45 degrees, and
   wherein the input light incident on the interference-light generator from the second optical path is a second linearly-polarized light having an inclination of +45 degrees or −45 degrees.

3. The sample clock generator for an optical tomographic imaging apparatus according to claim 2,
   wherein a first linear polarizer to transmit the first linearly-polarized light is disposed on an incident side of the optical phase shifter in the first optical path, and
   wherein a second linear polarizer to transmit the second linearly-polarized light and to make the transmitted second linearly-polarized light incident on the interference-light generator is disposed in the second optical path.

4. The sample clock generator for an optical tomographic imaging apparatus according to claim 2, the sample clock generator further comprising:
   a polarization-maintaining fiber coupler to branch the input light emitted from the light source and transmitted through a polarization controller performing linear polarization in a specified direction and to guide the first linearly-polarized light and the second linearly-polarized light to the first optical path and to the second optical path, respectively,
   wherein the first optical path at least comprises a first polarization-maintaining fiber to make the first linearly-polarized light incident on the optical phase shifter, and
   wherein the second optical path at least comprises a second polarization-maintaining fiber to make the second linearly-polarized light incident on the interference-light generator.

5. The sample clock generator for an optical tomographic imaging apparatus according to claim 2,
   wherein the optical phase shifter is a ¼ wavelength plate.

6. The sample clock generator for an optical tomographic imaging apparatus according to claim 1, the sample clock generator comprising:
   a first splitter on which a first interference light for sample clock is made incident from among the interference lights for sample clock emitted in two different directions from the interference-light generator, and that splits the first interference light for sample clock into a first one split light and a first the other split light, which have different phases from each other; and
   a second splitter on which a second interference light for sample clock is made incident, and that splits the second interference light for sample clock into a second one split light and the second the other split light, which have different phases from each other,
   wherein the first light receiver is a balanced photodetector on which the first one split light split by the first splitter and the second one split light split by the second splitter are made incident, and
   wherein the second light receiver is a balanced photodetector on which the first the other split light split by the first splitter and the second the other split light split by the second splitter are made incident.

7. The sample clock generator for an optical tomographic imaging apparatus according to claim 6,
   wherein the interference-light generator is a beam splitter to at least combine the input light guided through the first optical path and phase-shifted and the input light guided through the second optical path, to thereby generate the interference light for sample clock,
   wherein the first splitter is a first polarization beam splitter to at least split the first interference light for sample clock into a first one linearly-polarized light and a first the other linearly-polarized light, which are perpendicular to each other,
   wherein the second splitter is a second polarization beam splitter to at least split the second interference light for sample clock into a second one linearly-polarized light and a second the other linearly-polarized light, which are perpendicular to each other,
   wherein the first light receiver is a balanced photodetector on which the first one linearly-polarized light split by the first polarization beam splitter and the second one linearly-polarized light split by the second polarization beam splitter are made incident as the first one split light split by the first splitter and the second one split light split by the second splitter, respectively, and
   wherein the second light receiver is a balanced photodetector on which the first the other linearly-polarized light split by the first polarization beam splitter and the second the other linearly-polarized light split by the second polarization beam splitter are made incident as the first the other split light split by the first splitter and the second the other split light split by the second splitter, respectively.

8. The sample clock generator for an optical tomographic imaging apparatus according to claim 1,
wherein the first light receiver on which the first split light is made incident and the second light receiver on which the second split light is made incident are each a balanced photodetector, and
wherein the input light emitted from the light source is also made incident on the first light receiver and the second light receiver.

9. The sample clock generator for an optical tomographic imaging apparatus according to claim 1,
wherein the first optical path and the second optical path respectively have a first reflector and a second reflector provided therein that reflect the guided lights immediately,
wherein the first optical path and the second optical path are separated on a side from the interference-light generator to the first reflector and the second reflector, whereas overlap with each other on a side of the light source, the first light receiver, and the second light receiver,
wherein the splitter is disposed on a part in which the first optical path and the second optical path overlap each other,
wherein a light transmitted through the splitter in the input light emitted from the light source is made incident on the interference-light generator,
wherein a ⅛ wavelength plate, which is the optical phase shifter, is disposed between the first reflector to reflect a light transmitted through the interference-light generator and the interference-light generator,
wherein a ¼ wavelength plate is disposed between the second reflector to reflect a light reflected by the interference-light generator and the interference-light generator,
wherein the first light receiver at least receives at least the one linearly-polarized light obtained by splitting, by the splitter, the interference light for sample clock generated by the interference-light generating unit by combining the lights reflected by the first reflector and the second reflector, and
wherein the second light receiver at least receives the other linearly-polarized light obtained by splitting, by the splitter, the interference light for sample clock generated by the interference-light generator by combining the lights reflected by the first reflector and the second reflector.

10. The sample clock generator for an optical tomographic imaging apparatus according to claim 1,
wherein the interference-light generator is a beam splitter to at least combine the input light guided through the first optical path and phase-shifted and the input light guided through the second optical path, to thereby generate the interference light for sample clock,
wherein the splitter is a polarization beam splitter to at least split the interference light for sample clock into one linearly-polarized light and the other linearly-polarized light, which are perpendicular to each other,
wherein the first light receiver receives the one linearly-polarized light as the first split light, and
wherein the second light receiver receives the other linearly-polarized light as the second split light.

11. An optical tomographic imaging apparatus comprising:
a light source to emit a frequency-swept input light;
a measurement optical system to radiate an input light branched from the emitted input light on a specimen, and also to guide a reflected light reflected from the specimen;
a reference optical system that outputs the other branched light as a reference light;
a light receiver to receive a measurement interference light generated from the reflected light guided from the measurement optical system and the reference light from the reference optical system, and to output a measurement interference signal;
a sample clock generator comprising:
an interference optical system comprising:
a first optical path through which part of a frequency-swept input light emitted from a light source is guided;
a second optical path through which other part of the input light is guided;
an optical phase shifter to shift a phase of the input light guided through the first optical path;
an interference-light generator to combine the input light guided through the first optical path and phase-shifted and the input light guided through the second optical path, to thereby generate an interference light for sample clock; and
a splitter to split the interference light for sample clock into a first split light and a second split light having different phases; and
an operator at least comprising:
a first light receiver to at least receive the first split light;
a second light receiver to at least receive the second split light; and
a signal generator to generate a sample clock signal based on signals outputted from the first light receiver and the second light receiver; and
a signal processor to Fourier-analyze the measurement interference signal sampled based on the sample clock signal generated by the signal generator, and to acquire a tomographic image of the specimen through arithmetic processing.

* * * * *